United States Patent [19]

Ornstein

[11] Patent Number: 5,444,105
[45] Date of Patent: Aug. 22, 1995

[54] SPECIMEN MOUNTING ADHESIVE COMPOSITION

[75] Inventor: Leonard Ornstein, White Plains, N.Y.

[73] Assignee: Mount Sinai School of Medicine of the City University of New York, New York, N.Y.

[21] Appl. No.: 100,333

[22] Filed: Jul. 30, 1993

Related U.S. Application Data

[63] Continuation of Ser. No. 922,349, Jul. 29, 1992, abandoned, which is a continuation of Ser. No. 196,807, May 17, 1988, abandoned, which is a continuation of Ser. No. 852,592, Apr. 16, 1986, abandoned, which is a continuation of Ser. No. 417,254, Sep. 13, 1982, abandoned.

[51] Int. Cl.$^6$ ............................................. C08F 2/46
[52] U.S. Cl. ............................. 522/40; 522/90; 522/92; 528/48; 528/62; 528/64; 528/408
[58] Field of Search ............ 522/90, 40, 92; 528/48, 528/62, 64, 408

[56] References Cited

U.S. PATENT DOCUMENTS

| | | | |
|---|---|---|---|
| 3,450,613 | 6/1969 | Steinberg | 522/103 |
| 3,709,866 | 1/1973 | Waller | 522/96 |
| 3,803,109 | 4/1974 | Nemoto et al. | 522/90 |
| 4,052,282 | 10/1977 | Kubushiro | 522/90 |
| 4,120,991 | 10/1978 | Ornstein | 427/2 |
| 4,165,265 | 8/1979 | Nakabayashi | 522/93 |
| 4,287,255 | 9/1981 | Wong | 428/40 |
| 4,300,968 | 11/1981 | Fottinger | 522/174 |

*Primary Examiner*—Mark A. Chapman
*Attorney, Agent, or Firm*—Eugene Moroz

[57] ABSTRACT

A composition is disclosed for transferring and adhering tape-mounted histological sections, to specimen mounting surfaces, usually glass microscope slides to expedite and simplify the safe removal of the mounting tape and the subsequent processing of the slide-mounted section. The composition is a curable polymeric mixture which has high tack prior to curing, is substantially non-diffusable and non-flowable into tissue sections and, after curing, has a refractive index substantially similar to that of the specimen section and is non-labile to conventional histological solvents and stains. A preferred composition comprises diacrylate-terminated polyurethane, a diacrylate ester of an epoxy resin and a diethoxyacetophenone initiator. It is usually formed onto the mounting surface as a solution in a conventional organic solvent, such as isopropanol or toluene.

12 Claims, No Drawings

SPECIMEN MOUNTING ADHESIVE COMPOSITION

This is a continuation of co-pending application Ser. No. 922,349, filed on Jul. 29, 1992 now abandoned, which is a continuation of Ser. No. 196,807 filed May 17, 1988 now abandoned, which is a continuation of Ser. No. 852,592 now abandoned, which is a continuation of Ser. No. 417,254 filed Apr. 10, 1986, now abandoned.

BACKGROUND OF THE INVENTION

1. Field of the Invention

This invention relates to the field of biological specimen mounting, and more particularly to adhesives for such use.

2. Description of the Prior Art

Very thin slices of animal and plant tissue are prepared for many different kinds of microscopic studies by sectioning with a variety of kinds of microtomes. The tissue may be cut fresh. The soft and compliant nature of most fresh tissue makes it very difficult to cut undistorted thin sections. If the tissue is frozen and is cut on a freezing microtome or in a cryostat temperatures below 0° C. (32° F.), the hardness of the frozen water within the tissue permits sections to be cut relatively easily as thin as a few micrometers. However, these sections are brittle and friable and therefore difficult to handle and process further. To make sectioning of tissue still easier, a number of procedures produce a-block of supported tissue which has superior sectioning properties and produce high quality, relatively easy-to-handle tissue sections. Such procedures typically involve: (1) Fixation of the tissue in a solution which insolubilizes the natural polymers of which tissue cells are composed, and which hardens them; (2) dehydration through a series of water-miscible (e.g., an alcohol) and then paraffin or plastic-monomer-miscible (e.g., toluene or xylene) solvents; (3) infiltration in melted paraffin or monomer solution; and (4) embedding by freezing the paraffin or polymerizing the monomer to form a solid polymer. [*Staining Methods*, J. F. S. McManus and R. W. Mowry (P. B. Hoeber, Inc., N.Y. 1960); *Techniques for Electron Microscopy*, D. Kay, Ed. (Blackwell Sci. Publ., Oxford, England, 1965) pp. 166–212.]

However, there are occasional specimens which remain difficult to section. As the section is cut, the parts of the cut section often tend to fragment and fall from the cut section, or fall from the section as it is removed from the microtome.

A. Palmgren, *Nature*, Vol. 174, p. 46 (1954), introduced the use of a conventional adhesive tape as a sectioning aid for the cutting of very large, hard or brittle specimens. A piece of adhesive tape is applied to the surface of a cut frozen or paraffin block, just before the specimen is advanced the incremental thickness of a (next) section. The microtome advances and the next section is cut and is thus supported by the applied tape. The quality of the uncompressed section of hard brittle and friable tissue produced by this means can be far superior to that of a conventional section of the same block of tissue. However, following Palmgren, processing such a section while it remains on the tape, or transferring it to a glass slide (to permit it to be processed thereafter in a conventional way) involved elaborate, time-consuming and inconvenient methods, which are also potentially damaging to the section. Palmgren's method, therefore, did not become popular.

W. E. Beckel, *Nature*, Vol. 184, p. 1584 (1959) introduced the use of Scotch brand No. 810 cellulose-acetate-backed adhesive tape in Palmgren's process. The tape-mounted sections were applied, section-side down on conventionally wet albuminized glass slides. After thorough drying for a few hours, the adhesive backing, the adhesive layer and the paraffin were all dissolved in tetrahydrofuran in 30 minutes, leaving the section adhering to the glass slide, and available for further processing by conventional techniques. Alternatively, chloroform for 2 minutes, followed by xylene for 30 minutes, worked equally well. Beckel also described a "more rapid method" which used a film of albumin and a solution of 2 per cent celloidin in methyl benzoate or ethyl alcohol to "cement" the section to the glass slide followed by 1 minute in chloroform and 10 minutes in xylene to complete the treatment. Some other equally time-consuming variations were described.

D. S. Gowers and R. E. Miller, *Nature*, Vol. 190, p. 425 (1961), attempted to repeat Beckel's method but found that, with available Scotch brand No. 810 tape, the adhesive could not be dissolved, and with the best alternate available tape, Tuck brand No. 200, safe removal of the tape without damaging the section in solvent took from 1 to 10 hours.

R. P. Wedeen and H. I. Jernow, *Am. J. Physiol.*, Vol. 214, p. 776 (1968) used cyanoacrylate (Eastman 910 "super-glue") to attach adhesive-tape-supported frozen sections to radioautographic (photographic) plates. The cyanoacrylate is initially liquid, but polymerizes to a solid when it is squeezed out into a thin film. The cyanoacrylate polymer is soluble in xylene and other processing solvents, which would cause the section to float free, and so is not useful for ordinary use.

In another area of study relating to the field of specimen section handling, various resinous mounting media have been developed. After the tissue section has been stained, the slide is transferred from water through alcoholic and then resincompatible solvents, such as xylene, and the section is mounted in a resinous medium chosen to have a refractive index which closely approximates the average refractive index of the unstained tissue specimens, e.g., a refractive index from about 1.530 to about 1,570. Such are described, for example, in U.S. Pat. No. 4,120,991, and McManus & Mowry, above.

SUMMARY OF THE INVENTION

To achieve heretofore unavailable advantages which expedite and simplify the processing of tape-mounted specimen sections, the invention provides curable adhesive composition for transferring and mounting a tape-supported tissue specimen onto a specimen support, comprising at least one polymerizable component and a polymerization curing initiator therefor and which composition has the following characteristics:

a. is a high tack pressure-sensitive adhesive prior to cure;

b. has a sufficiently low diffusion coefficient before cure to substantially prevent diffusion into tissue;

c. has a viscosity which is sufficiently high before cure to substantially prevent flow into tissue during specimen application to said specimen support;

d. is rapidly cured;

e. is substantially non-swelling; tack-free, insoluble, unreactive and non-ionic after cure;

f. has a cured refractive index between about 1.53 and about 1.56; and g. after cure, bonds strongly to both the specimen surface and support surface.

Such curable adhesive composition is typically coated onto a glass microscope slide. A cut paraffin embedded section, supported on adhesive tape, is pressed, section-side down, onto the adhesive-coated glass microscope slide. The contact is assured by smoothing with moderate finger pressure. The laminate, bottom-of-the-glass-side up, is placed within a few inches of a 4-watt black-light fluorescent lamp with a phosphor peaklight output near 350 nm, for 3 minutes. The laminate is then immersed in a solvent, such as xylene, and the adhesive tape is gently peeled away over a period of about 5 seconds. The very strong bond between the bottom of the section and the glass slide make this otherwise critical step very easy. The solvent greatly weakens the tape-adhesive-to-tissue and the tape-adhesive-to-tape-backing bonds. Any remaining adhesive layer from the tape and the paraffin are dissolved away in about one minute with gentle agitation, and the slide is ready for processing in the conventional manner. However, for a detailed description of the method, reference is made to my U.S. Ser. No. 06/417,387 now abandoned, filed on Sep. 13, 1982.

DESCRIPTION OF THE PREFERRED EMBODIMENTS

In a preferred embodiment, the composition of the present invention is a curable polymeric mixture which has the high tack of a pressure-sensitive adhesive prior to curing, is substantially non-diffusable into tissue sections and, after curing, has a refractive index substantially similar to that of the tissue section and is non-labile to conventional histological solvents and stains. A preferred composition comprises a diacrylateterminated polyurethane, a diacrylate ester of an epoxy resin and a diethoxyacetophenone initiator. It is usually formed onto the mounting surface of the specimen support as a solution in a conventional organic solvent, such as toluene or isopropanol.

The preferred composition suitable to achieve the above objectives comprises a mixture of high molecular weight interreactive oligomers. The high molecular weight assures both high viscosity and low diffusion coefficient. The upper limitation of the molecular weight is such that there remains high tack in the pre-cured mixture when coated on a mounting surface. In one preferred embodiment, the mixture includes a first oligomer having a cured refractive index above 1.560 and another that has a cured refractive index less than 1,530, for example, an oligomeric diacrylate ester of an epoxy resin and a polyurethane diacrylate oligomer, respectively. Both cured resins must be resistant to histological stains and solvents. Preferably, both resins are provided with terminal acryl or methacryl groups to permit radical initiated cross-linked polymerization. These oligomer resins are mixed in proportions, more fully described below, which provide a cured refractive index between about 1.530 and about 1.560, using the Dale-Gladstone equation described in standard physical chemistry texts and procedures.

Components particularly preferred in forming the composition of the invention include those of low refractive index such as diacrylate-terminated polyurethanes, including Purelast 190, 186 and 169, available from Polymer Systems Corporation, Little Falls, N.J., in combination with those of high refractive index such as diacrylate esters of epoxy resins, such as Epicryl 370 resin and Shell Developmental Polyester Resin DRH 301.1, both available from Shell Corporation, a division of Shell Oil Company, Houston, Tex.

A further essential component of the composition is an initiator, such as a thermal initiator or preferably a photoinitiator. A thermal initiator, such as benzoyl peroxide, acetylperoxide or azoisobutyronitrile may be included, if curing is to be effected thermally. When cured in this manner, it is preferable to add the initiator just prior to curing. The thermal treatment is effectively achieved by heating at a temperature from about 40° C. to about 200° C. Alternatively, a broad spectrum of photoinitiators can be used including benzoin and acetophenones such as 2,2-dimethoxy-2-phenylacetophenone and 2,2-diethoxyacetophenone. The preferred photoinitiator for use with the above polymer mixture is 2,2-diethoxyacetophenone, available from the Upjohn Company, Fine Chemical Division, New Haven, Connecticut. Toluene and isopropanol are standard commercially available reagent grade solvents.

Typical proportions of the epoxy ester to the urethane resin is from about 2:1 to about 3:1 by weight. The ratio of the combined resins to the initiator component is approximately 20:1 by weight. About 0.5 grams per milliliter of the mixture of the above two resins in an appropriate solvent is preferred.

Other combinations of reactive oligomer and/or polymer systems such as yield epoxy resins, polyurethanes, polyesters, etc., with other initiators and solvents can be formulated by those skilled in the art to fill the requirements in the listed specifications.

The composition of the invention is suitable for layering on specimen supports such as glass microscope slides. It can be layered by printing, spraying or spreading in film-forming solvents which thereafter evaporate. In one preferred embodiment, the composition is coated by hand, using a blade coating device, or by machine, using techniques such as dip or bead coating. If machine coating is used, hopper coating techniques, such as are known in the photographic industry, are preferred.

The thickness of any layer and its degree of permeability are widely variable and dependent on actual use. Dry thickness of the adhesive prior to curing is from about 10 to about 25 micrometers.

What is claimed is:

1. A highly viscous and substantially indiffusible curable adhesive composition for transferring and mounting a tape-supported thin histological tissue section onto a specimen support for further processing, comprising a high molecular weight polymerizable component wherein said component contains one or more high molecular weight polymerizable interractive difunctional oligomers selected from acryl or methacryl esters of epoxy resins or mixtures thereof with acryl- or methacryl-terminated polyurethane resins, and a polymerization curing initiator therefor, which polymerized composition is characterized in that before cure:
   a. it is a high tack pressure-sensitive adhesive having a viscosity greater than $10^5$ cps at the temperature of use;
   b. it does not substantially diffuse into a thin tissue section at the temperature of use;
   c. it does not substantially flow into said tissue section at the temperature of use;
   d. it is rapidly curable, and after cure;
   e. it is substantially non-swelling, tack-free, insoluble, unreactive and non-ionic;

f. it has a refractive index between about 1.53 and about 1.56; and g. it bonds strongly to both the surface of said thin tissue section and said support surface.

2. The composition of claim 1 wherein the epoxy ester and the urethane resin are present in a ratio of from about 2:1 to about 3:1 by weight.

3. The composition of claim 1 wherein said polymerization curing initiator is a photoinitiator.

4. The composition of claim 3 wherein said photoinitiator is selected from the group consisting of benzoin and acetophenones.

5. The composition of claim 4 wherein said acetophenone is 2,2-dimethoxy-2-phenylacetophenone.

6. The composition of claim 5 wherein said acetophenone is 2,2-diethoxyacetophenone.

7. The composition of claim 1 wherein said polymerization curing initiator is a thermal initiator.

8. The composition of claim 1 wherein said thermal initiator is benzoyl peroxide.

9. The composition of claim 1 wherein said thermal initiator is acetylperoxide.

10. The composition of claim 1 wherein said thermal initiator is azoisobutyronitrile.

11. The composition of claim 1 wherein said component comprises a mixture of a diacrylate-terminated urethane and a diacrylate ester of an epoxy resin.

12. A highly viscous and substantially indiffusible curable unpolymerized adhesive composition for transferring and mounting a tape-supported thin histological tissue section onto a specimen support for further processing, comprising a mixture of diacrylate-terminated urethane and a diacrylate ester of an epoxy resin in a weight ratio of 1:2 to about 1:3 respectively, said composition further comprising a polymerizable curing initiator therefor, which composition is characterized in that before cure:

a. it is a high tack pressure-sensitive adhesive having a viscosity greater than $10^5$ cps at the temperature of use;

b. it does not substantially diffuse into a thin tissue section at the temperature of use;

c. it does not substantially flow into said tissue section at the temperature of use;

d. it is rapidly curable, and after cure;

e. it is substantially non-swelling, tack-free, insoluble, unreactive and non-ionic; and f. it bonds strongly to both the surface of said thin tissue section and said support surface.

* * * * *